United States Patent [19]

Okawa et al.

[11] Patent Number: 5,262,506
[45] Date of Patent: * Nov. 16, 1993

[54] ORGANOPOLYSILOXANE AND METHOD FOR ITS PREPARATION

[75] Inventors: Tadashi Okawa; Shuji Yamada, both of Chiba, Japan

[73] Assignee: Dow Corning Toray Silicone Co., Ltd., Tokyo, Japan

[*] Notice: The portion of the term of this patent subsequent to Jun. 2, 2009 has been disclaimed.

[21] Appl. No.: 871,249

[22] Filed: Apr. 20, 1992

[30] Foreign Application Priority Data

Apr. 23, 1991 [JP] Japan .................................. 3-119411

[51] Int. Cl.$^5$ .............................................. C08G 77/26
[52] U.S. Cl. ........................................ 528/27; 528/31; 528/26; 528/28; 528/38; 528/41; 549/215; 556/425; 556/434; 556/435
[58] Field of Search ................ 549/215; 556/425, 434, 556/435, 438, 440; 528/15, 27, 28, 26, 38, 41

[56] References Cited

U.S. PATENT DOCUMENTS

| | | | |
|---|---|---|---|
| 3,819,674 | 6/1974 | Rudolph et al. | 556/434 |
| 4,208,503 | 6/1980 | Martin | 549/215 |
| 4,617,340 | 10/1986 | Tanaka et al. | 524/588 |
| 4,990,546 | 2/1991 | Eckberg | 522/170 |
| 5,041,591 | 8/1991 | Okawa | 556/434 |
| 5,118,777 | 6/1992 | Okawa | 528/34 |

FOREIGN PATENT DOCUMENTS 412550 2/1991 European Pat. Off. ............ 556/434

Primary Examiner—Ralph H. Dean
Attorney, Agent, or Firm—James L. DeCesare

[57] ABSTRACT

There is described an organopolysiloxane which contains at least 2 amino groups, carboxyl groups, hydroxyl groups, or epoxy-functional organic groups at one and only one molecular chain terminal, as well as a method for the preparation of same. The organopolysiloxane has the formula

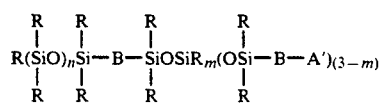

wherein R is a monovalent hydrocarbon group which is free of aliphatically unsaturated bonds and wherein the groups R may be identical or different; A' is selected from the group consisting of groups, the carboxyl group, the hydroxyl group, and epoxy-functional organic groups; B is the same or a different divalent organic group having at least 2 carbon atoms; m is zero or one; and n is an integer with a value of zero to 200.

3 Claims, 4 Drawing Sheets

ORGANOPOLYSILOXANE AND METHOD FOR ITS PREPARATION

BACKGROUND OF THE INVENTION

The present invention relates to a novel organopolysiloxane and method for the preparation of same. More specifically, the present invention relates to an organopolysiloxane which bears at least two amino groups, carboxyl groups, hydroxyl groups, or epoxy-functional organic groups at one and only one of its molecular chain terminals, and to a method for the preparation of same.

Organofunctional group-containing ("organofunctionalized") organopolysiloxanes are employed in a wide range of fields as a fiber-treatment agent and as a modifying agent for organic resins. This type of organopolysiloxane is prepared by an addition reaction between SiH-containing organopolysiloxane and an organofunctionalized, aliphatically unsaturated hydrocarbon compound in the presence of a hydrosilylation-reaction catalyst. The number of organofunctional groups in the organopolysiloxane afforded thereby and its chemical structure are dictated by the SiH-containing organopolysiloxane employed as starting material.

In recent years, it has become necessary in the field of fine chemistry to control the number of organofunctional groups in organopolysiloxanes and the chemical structure of organopolysiloxanes. A particularly precise control of these parameters is required when the organopolysiloxane is to be employed as a modifier for organic resins.

However, the number of silicon-bonded hydrogens and the chemical structure in the SiH-containing organopolysiloxane precursor are both variable when this material is produced by an ionic equilibrium polymerization reaction. As a result, organopolysiloxanes prepared from such a starting material also have a variable number of organofunctional groups and a variable chemical structure. When such an organopolysiloxane is employed as a modifier for an organic resin, the effects deriving from modification in the organic resin afforded thereby are unsatisfactory.

On the other hand, the preparation of variously organofunctionalized organopolysiloxanes by a nonequilibrium polymerization reaction has been introduced. For example, in order to prepare an organopolysiloxane carrying organofunctionality at a single molecular chain terminal, a ring-opening polymerization is first run on hexaorganocyclotrisiloxane using alkyllithium or lithium silanolate as initiator. Stopping this reaction with dimethylchlorosilane affords an organopolysiloxane carrying silicon-bonded hydrogen at only one molecular chain terminal, which is subsequently addition-reacted with an organofunctionalized aliphatically unsaturated hydrocarbon compound in the presence of a hydrosilylation-reaction catalyst to afford the target material.

However, a drawback to this technique is that it affords only an organopolysiloxane carrying a single organofunctional group at the one molecular chain terminal.

With regard to the organopolysiloxane bearing at least 2 organofunctional groups at one and only one molecular chain terminal, Japanese Patent Application Laid Open [Kokai or Unexamined] Number 62-195389 [195,389/87] discloses an organopolysiloxane bearing the dicarbinol group at a single molecular chain terminal.

A problem with the organopolysiloxane disclosed in Japanese Patent Application Laid Open Number 62-195389 is that the organofunctional group is limited to the carbinol group.

SUMMARY OF THE INVENTION

The present invention takes as its object the introduction of an organopolysiloxane which is free of the aforementioned problems because it carries at least 2 amino groups, carboxyl groups, hydroxyl groups, or epoxy-functional organic groups at one and only one molecular chain terminal.

The aforesaid object of the present invention can be accomplished by an organopolysiloxane with the formula

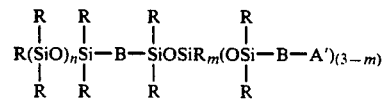

in which R is a monovalent hydrocarbon group free of aliphatically unsaturated bonds and wherein the groups R may be identical or different; A' is selected from the group consisting of amino groups, the carboxyl group, the hydroxyl group, and epoxy-functional organic groups; B is the same or a different divalent organic group having at least 2 carbon atoms; m is zero or one; and n is an integer with a value of zero to 200.

DETAILED DESCRIPTION OF THE INVENTION

Figure 1:
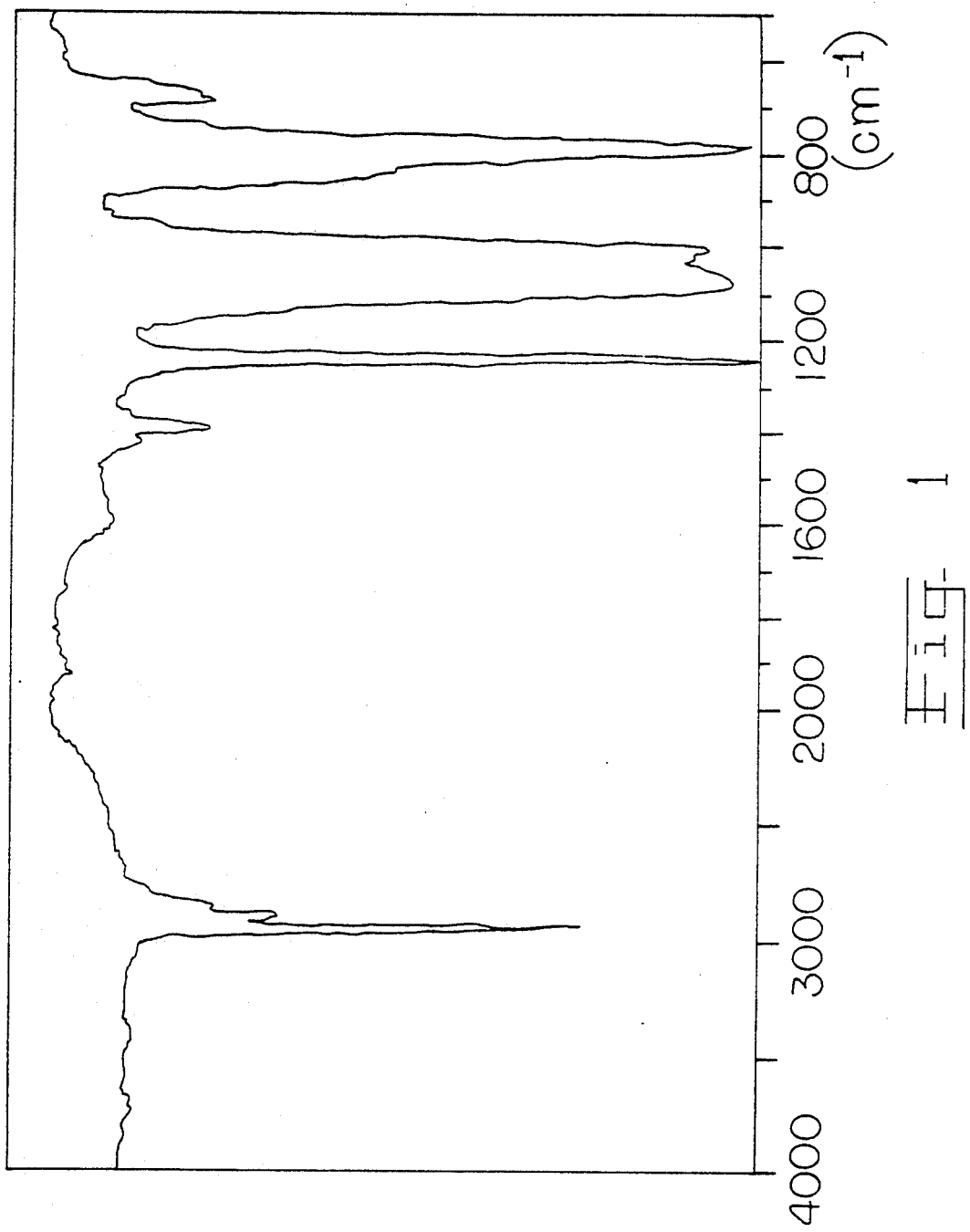
FIG. 1 contains the IR spectrogram of the organopolysiloxane prepared in Example 1.
Figure 2:
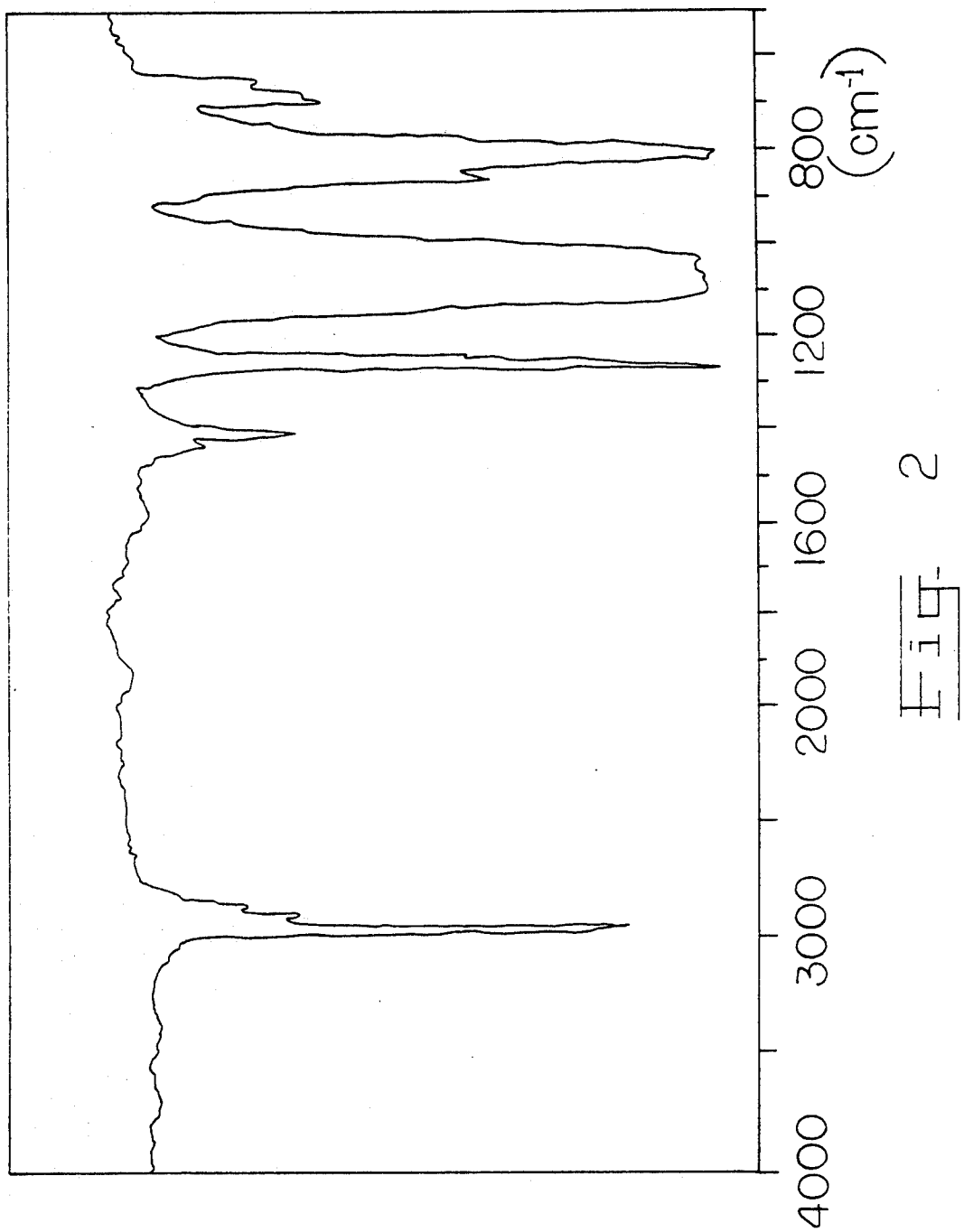
FIG. 2 contains the IR spectrogram of the organopolysiloxane prepared in Example 4.
Figure 3:
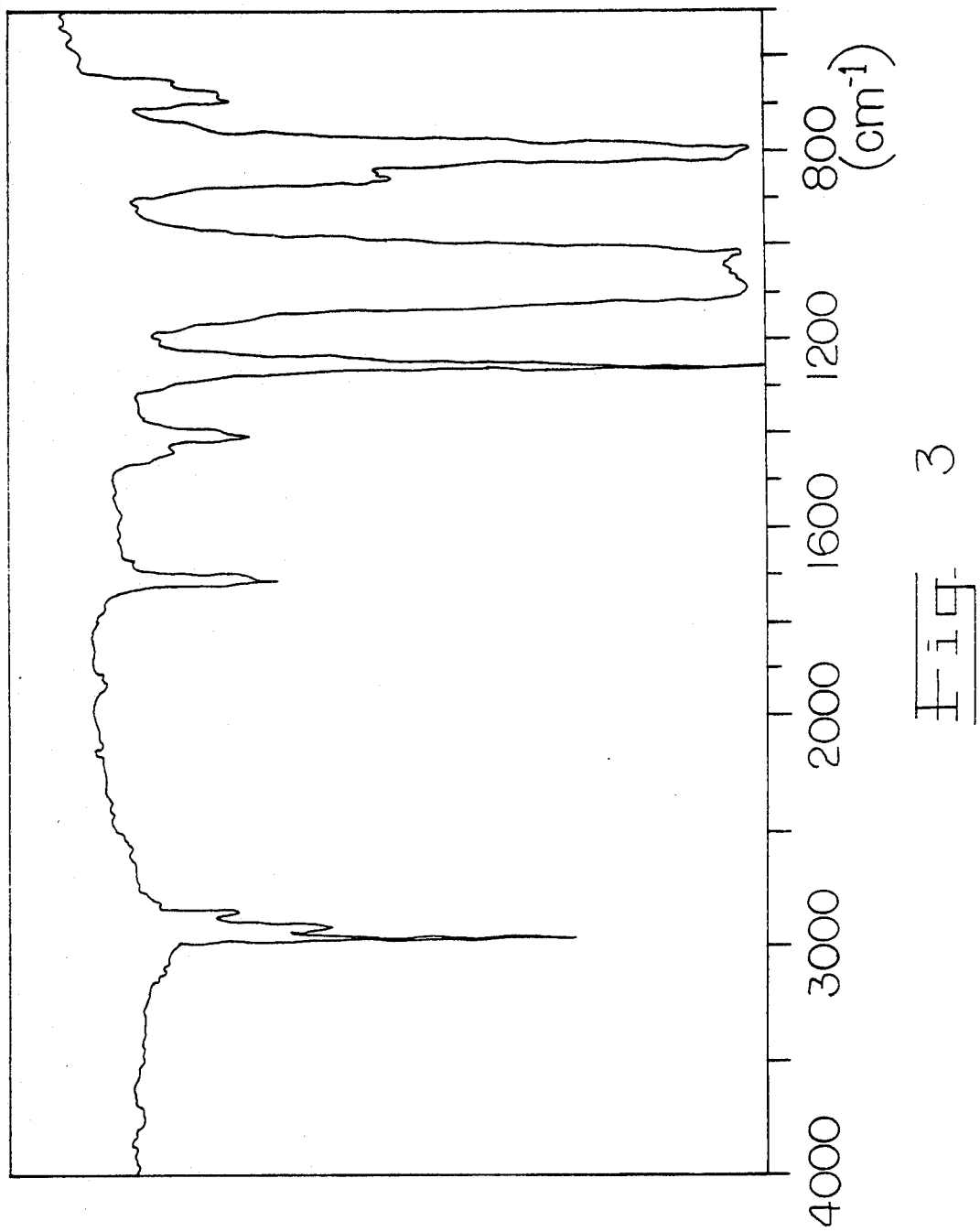
FIG. 3 contains the IR spectrogram of the organopolysiloxane prepared in Example 5.
Figure 4:
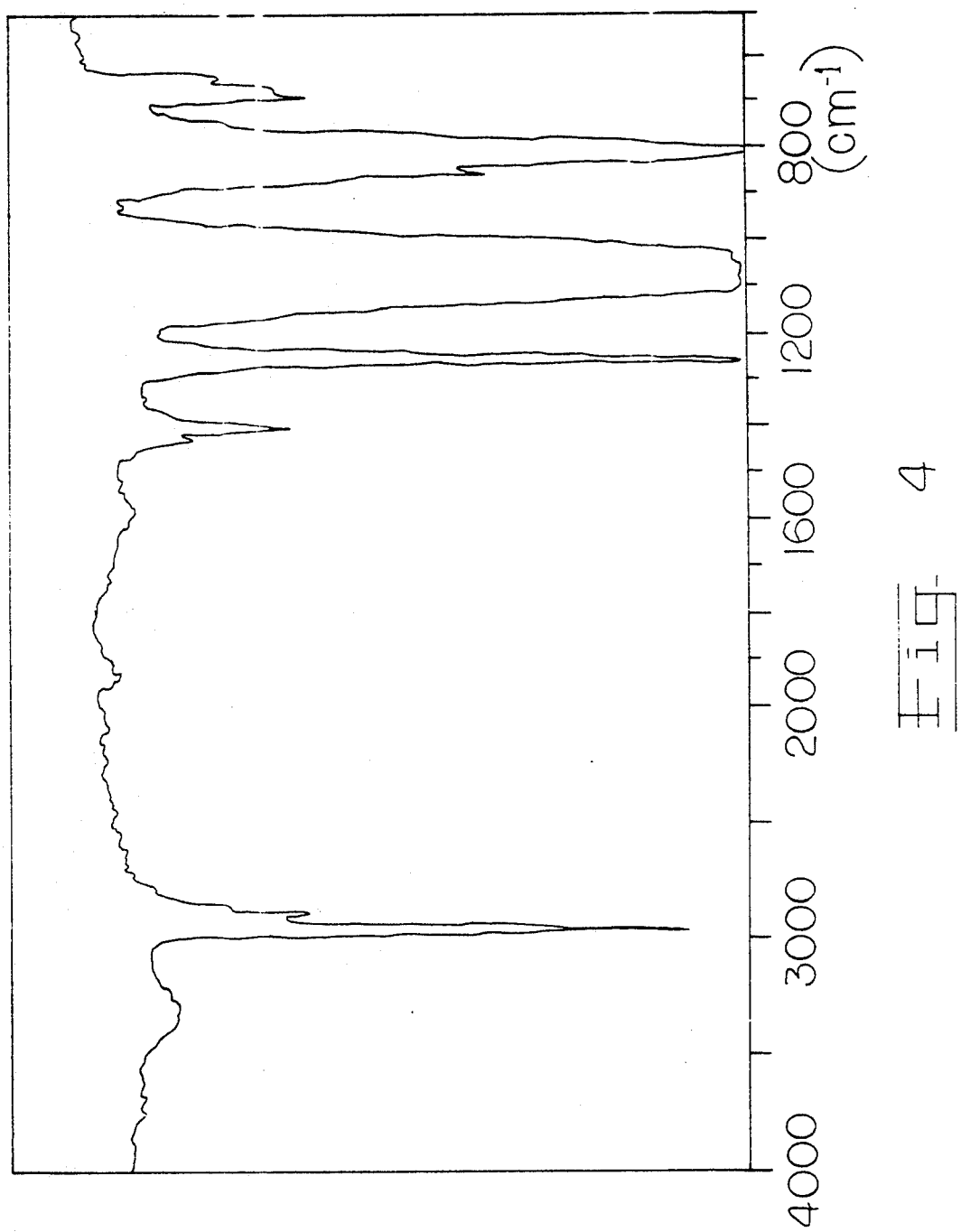
FIG. 4 contains the IR spectrogram of the organopolysiloxane prepared in Example 6.

The organopolysiloxane according to the present invention is explained in greater detail below.

The organopolysiloxane according to the present invention is expressed by the following formula.

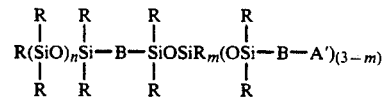

The group R in this formula comprises a single species or multiple species of monovalent hydrocarbon group free of aliphatically unsaturated bonding, and this group is exemplified by alkyl groups such as methyl, ethyl, propyl, butyl, pentyl, and hexyl; aryl groups such as phenyl, tolyl, and xylyl; and aralkyl groups such as benzyl and phenethyl. R is preferably methyl from the standpoints of ease of synthesis and economic efficiency. A' is selected from the group consisting of amino groups, the carboxyl group, the hydroxyl group, and epoxy-functional groups, and this group is exemplified by amino groups such as the amino group itself, cyclohexenylamino, and aminoethylamino; by the carboxyl group; and by the hydroxyl group. B is a divalent organic group having at least 2 carbon atoms, and this group is exemplified by alkylene groups such as ethylene, propylene, butylene, pentylene, and hexylene, and by alkyleneoxyalkylene groups such as ethyleneoxypropylene and ethyleneoxybutylene. The group B is preferably ethylene, propylene, or butylene from the standpoints of ease of synthesis and economic efficiency. The subscript m has values of zero or one. When m=zero, the organopolysiloxane according to the present invention carries 3 of the aforementioned organofunctional groups at the one molecular chain terminal. When m=one, the organopolysiloxane according to the present invention carries 2 of the aforementioned organofucntional groups at the one molecular chain terminal. The subscript n is an integer with a value of 0 to 200. An organopolysiloxane with n>200 has a reduced copolymerizability with an organic resin monomer in its application as a modifying agent for organic resins. n is preferably 0 to 100 and is particularly preferably 5 to 90.

The organopolysiloxane according to the present invention can be prepared by the methods discussed below.

In the first case, an organopolysiloxane carrying groups selected from the group consisting of amino groups, the carboxyl group, and the hydroxyl group at one and only one molecular chain terminal, can be prepared by first running an addition reaction, in the presence of a hydrosilylation-reaction catalyst, between an organopolysiloxane with the formula

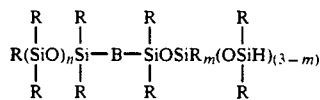

in which R is a monovalent hydrocarbon group which is free of aliphatically unsaturated bonds and wherein the groups R may be identical or different, B is a divalent organic group having at least 2 carbon atoms, m is zero or one, and n is an integer with a value of zero to 200; and an aliphatically unsaturated hydrocarbon compound which contains a triorganosilyl-blocked amino group, triorganosilyl-blocked carboxyl group, or triorganosilyl-blocked hydroxyl group; and by the subsequent execution of a de-triorganosilylation reaction thereon.

The organopolysiloxane with the formula

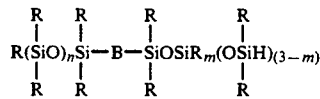

which is employed in the aforesaid preparative method according to the present invention is the primary starting material, and comprises an organopolysiloxane carrying at least 2 silicon-bonded hydrogen atoms at one and only one molecular chain terminal. In the preceding formula, R is a monovalent hydrocarbon group as defined above, and B is a divalent organic group having at least 2 carbons also as defined above. The subscript m is zero or one, and the subscript n is an integer with a value of 0 to 200.

This organopolysiloxane with the formula

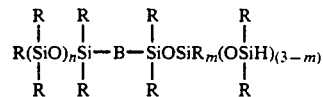

can itself be prepared by (a) addition-reacting an organopolysiloxane carrying 1 silicon-bonded hydrogen at one molecular chain terminal with an aliphatically unsaturated organodichlorosilane or with an aliphatically unsaturated trichlorosilane in the presence of a hydrosilylation-reaction catalyst, followed by (b) hydrolysis of the product and reaction with a diorganochlorosilane.

This preparative method according to the present invention also employs an aliphatically unsaturated hydrocarbon compound which contains a triorganosilyl-blocked amino group, a triorganosilyl-blocked carboxyl group, or a triorganosilyl-blocked hydroxyl group. Examples in this regard are trimethylsilylallylamine, trimethylsilyallylcyclohexenylamine, and trimethylsilylpropylallylamine for the aliphatically unsaturated hydrocarbon compound bearing a triorganosilyl-blocked amino group; trimethylsilyl undecenoate, trimethylsilyl octenoate, and trimethylsilyl decenoate for the aliphatically unsaturated hydrocarbon compound bearing the triorganosilyl-blocked carboxyl group; and trimethylallyloxysilane and trimethylisobutenyloxysilane for the aliphatically unsaturated hydrocarbon compound bearing the triorganosilyl-blocked hydroxyl group.

This aliphatically unsaturated hydrocarbon compound should be deployed in this preparative method according to the present invention in a quantity which will provide at least one equivalent of unsaturated bonds in said aliphatically unsaturated hydrocarbon compound per silicon-bonded hydrogen atom in the organopolysiloxane carrying SiH at the single molecular chain terminal.

The preparative method according to the present invention may be executed by first running an addition reaction, in the presence of a hydrosilylation-reaction catalyst, between a organopolysiloxane with the formula

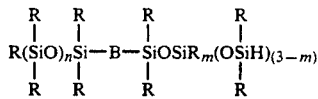

and an aliphatically unsaturated hydrocarbon compound carrying the triorganosilyl-blocked amino group, the triorganosilyl-blocked carboxyl group, or the triorganosilyl-blocked hydroxyl group. Subsequent to this the reaction, unreacted aliphatically unsaturated hydrocarbon compound is vacuum distilled with heating, the protective triorganosilyl group is hydrolyzed or alcoholyzed, and, finally, by-product is distilled out in vacuo with heating.

The triorganosilyl group is exemplified by trimethylsilyl, triethylsilyl, phenyldimethylsilyl, and tert-butyldimethylsilyl, but trimethylsilyl is preferred as the triorganosilyl group based on its ease of acquisition and good de-triorganosilylation reaction rate. This de-triorganosilylation reaction is readily executed as a hydrolysis or alcoholysis; however, methanolysis is preferred for the associated high reaction selectivity and facile separation and purification. When the organofunctional group is a triorganosilyl-blocked amino group or a triorganosilyl-blocked carboxyl group, the methanol-based de-triorganosilylation reaction will proceed readily even at room temperature, but the reaction mixture is preferably heated to approximately 50° C. in order to raise the reaction rate and bring the de-triorganosilylation reaction to completion. Because the de-triorganosilylation reaction is an equilibrium reaction when the organofunctional group is the hydroxyl group, the reaction in this case is preferably run using a catalyst, while shifting the equilibrium to the product side through the addition of a large excess of methanol with heating, and distillation of the trimethylmethoxysilane by-product from the system. The catalyst is exemplified by organic acids such as acetic acid and propionic acid; inorganic acids such as carbonic acid, hydrochloric acid, and sulfuric acid; inorganic bases such as sodium hydroxide, potassium hydroxide, and lithium hydroxide; and amines such as triethylamine, pyridine, and quinoline. Among these, the carboxylic acids are preferred, and acetic acid and propionic acid are particularly preferred, because they exercise a high catalytic activity, are easy to remove from the post-reaction system by distillation, and are associated with little siloxane chain cleavage reactivity.

The hydrosilylation-reaction catalyst used by this preparative method according to the present invention generally comprises a catalyst which accelerates the hydrosilylation reaction. Platinum-type catalysts are particularly preferred, and examples here are chloroplatinic acid, alcohol solutions of chloroplatinic acid, platinum/olefin complexes, platinum/vinylsiloxane complexes, platinum-on-silica, and platinum-on-active carbon.

In the second case, an organopolysiloxane carrying epoxy-functional groups at one and only one molecular chain terminal can be prepared by an addition reaction, in the presence of a hydrosilylation-reaction catalyst, between an organopolysiloxane with the formula

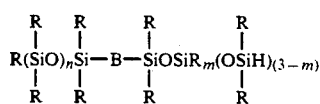

wherein R is a monovalent hydrocarbon group which is free of aliphatically unsaturated bonds and wherein the groups R may be identical or different, B is a divalent organic group having at least 2 carbon atoms, m is zero or one, and n is an integer with a value of zero to 200; and an aliphatically unsaturated hydrocarbon compound bearing an epoxy-functionalized organic group.

The organopolysiloxane with the formula

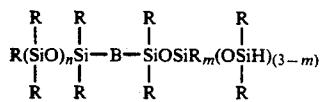

used in this preparative method according to the present invention is the primary starting material, and comprises the same organopolysiloxane as above.

The epoxy-functionalized unsaturated hydrocarbon compound used by this preparative method according to the present invention is exemplified by allyl glycidyl ether and 3,4-epoxycyclohexylethene.

This aliphatically unsaturated hydrocarbon compound should be deployed in this preparative method according to the present invention in a quantity which will provide at least one equivalent of unsaturated bonds in said aliphatically unsaturated hydrocarbon compound per silicon-bonded hydrogen atom in the organopolysiloxane carrying SiH at the single molecular chain terminal.

The same catalyst as described hereinbefore can be used as the hydrosilylation-reaction catalyst in this preparative method according to the present invention.

The preparative methods according to the present invention can be implemented in the presence or absence of solvent. Usable solvents in this regard are exemplified by aromatic solvents such as benzene, toluene, and xylene; aliphatic solvents such as hexane and heptane; ether solvents such as tetrahydrofuran and diethyl ether; ketone solvents such as acetone and methyl ethyl ketone; ester solvents such as ethyl acetate and butyl acetate; chlorinated hydrocarbon solvents such as carbon tetrachloride, trichloroethane, and chloroform; and dimethylformamide and dimethyl sulfoxide.

The preparative method according to the present invention can be run at room temperature, but in general is preferably run at 50° C. to 200° C. in order to obtain a favorable reaction rate.

Due to the presence of least 2 organofunctional groups at one and only one molecular chain terminal, when the organopolysiloxane according to the present invention is employed for the modification of an organic resin through a copolymerization reaction with an organic resin monomer, an organic resin is produced in which the organopolysiloxane is bonded in a graft configuration. This leads to an improvement in the modifying effect on the organic resin.

The present invention is explained in greater detail in the following demonstrative examples and reference examples.

REFERENCE EXAMPLE 1

A mixture of 240 mL isopropyl alcohol, 120 mL concentrated hydrochloric acid, and 240 mL water was cooled with ice water to below 10° C., and 120.6 g (900 mmol) 1,1,3,3-tetramethyldisiloxane was then introduced, and 54.5 g (400 mmol) methyltrimethoxysilane was subsequently dripped in. After removing the ice-water bath and stirring for 1 hour, the aqueous layer was discarded, and the organic layer was neutralized by the addition of sodium bicarbonate. After repeatedly washing with water until the aqueous layer reached neutrality, the organic layer was dried over sodium sulfate and then subjected to vacuum distillation to afford 45.5 g graction at 97°-98° C./83 mmHg. Analysis of this fraction by $^1$H nuclear magnetic resonance analysis (NMR) and by infrared spectrochemical analysis (IR) confirmed it to be methyltris(dimethylsiloxy)silane.

The following were introduced into a stirrer-equipped four-neck flask and heated to 80° C.: 120 g (446.15 mmol) methyltris(dimethylsiloxy)silane and sufficient platinum/tetramethyldivinyldisiloxane complex to afford 20 ppm platinum metal referred to the total quantity of the reaction mixture. Dimethylvinylchlorosilane (21.5 g) was dripped in followed by stirring for 1 hour with heating to 90°-100° C. The reaction was assumed to be complete at this point due to the disappearance of the peak for the starting dimethylvinylchlorosilane in analysis by gas chromatography (GLC). Collection of the fraction at 89°–91° C./1 mmHg in vacuum distillation afforded 47.6 g product (polymer T-1). Analysis of polymer T-1 by NMR and IR confirmed it to be a chlorosilicone compound with the following structural formula.

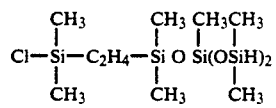

Into a stirrer-equipped four-neck flask were introduced 60 g (270.3 mmol) hexamethylcyclotrisiloxane and 60 g tetrahydrofuran, and the liquid temperature was cooled with ice water to below 20° C. An n-hexane solution of 32.43 mmol n-butyllithium was introduced with stirring under a dry nitrogen blanket followed by stirring at room temperature. The development of the polymerization was monitored by GLC. The conversion reached 98.4% after 6 hours, at which point the polymerization was stopped by the addition first of 0.66 g (6.5 mmol) triethylamine and then 13.89 g (35.68 mmol) polymer T-1. The salt by-product was filtered off, and the solvent and low boilers were vacuum distilled with heating to afford a colorless, transparent polymer. This was confirmed by NMR, IR, and GPC analyses and iodometric determination of SiH group weight %, to be an organopolysiloxane with the following average formula (polymer P-1).

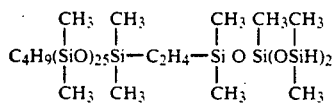

SiH group weight %: measured value=0.093%
(calculated value=0.090%)
number-average molecular weight: 2,288
dispersivity: 1.13

REFERENCE EXAMPLE 2

An organopolysiloxane with the average formula given below (polymer P-2) was prepared as in Reference Example 1 using 420 g (1,891.9 mmol) hexamethylcyclotrisiloxane, 420 g tetrahydrofuran, 119.19 mmol n-butyllithium, 2.3 g (22.72 mmol) triethylamine, and 46.91 g (119.19 mmol) polymer T-1.

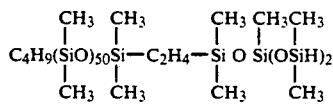

SiH group weight %: measured value=0.051%
(calculated value=0.049%)
number-average molecular weight: 4,616
dispersivity: 1.10

REFERENCE EXAMPLE 3

An organopolysiloxane with the average formula given below (polymer P-3) was prepared as in Reference Example 1 using 60 g (27.03 mmol) hexamethylcyclotrisiloxane, 60 g tetrahydrofuran, 16.22 mmol n-butyllithium, 0.22 g (2.17 mmol) triethylamine, and 4.63 g (11.89 mmol) polymer T-1.

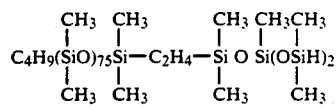

SiH group weight %: measured value=0.034%
(calculated value=0.034%)
number-average molecular weight: 7,218
dispersivity: 1.08

EXAMPLE 1

The following were combined: 30 g polymer P-1 (SiH: 27.9 milliequivalents), 5.41 g (41.88 mmol) trimethylsilylallylamine, and sufficient platinum/tetramethyldivinyldisiloxane complex to give 50 ppm platinum metal referred to the preceding two reactants. After heating at 100° C. for 2 hours, a sample was taken, and disappearance of the absorption characteristic of the SiH group was confirmed in infrared spectrochemical analysis. The low boilers were distilled off in vacuo with heating to afford a transparent liquid, which was confirmed by NMR and IR analyses to be organopolysiloxane with the following structural formula.

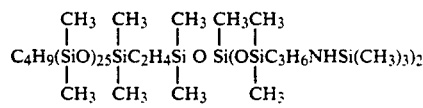

This organopolysiloxane (30 g) was stirred at 50° C. for 3 hous with 7.97 g methanol. The low boilers were then distilled off in vacuo with heating to afford a transparent liquid, which was confirmed by NMR and IR analyses and determination of the amino group weight %, to be an organopolysiloxane with the following structural formula.

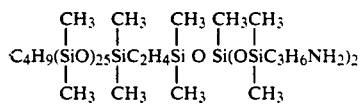

NH$_2$ group weight %: measured value=1.33%
(calculated value=1.33%)

EXAMPLE 2

An organopolysiloxane with the structural formula given below was prepared as in Example 1 using 50 g polymer P-2 (SiH: 25.3 milliequivalents) and 4.24 g (31.25 mmol) trimethylsilylallylamine.

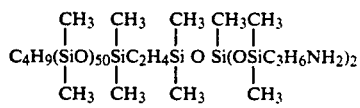

NH$_2$ group weight %: measured value=0.78%
(calculated value=0.76%)

EXAMPLE 3

An organopolysiloxane with the structural formula given below was prepared as in Example 1 using 40 g polymer P-3 (SiH: 13.6 milliequivalents) and 2.2 g (16.27 mmol) trimethylsilylallylamine.

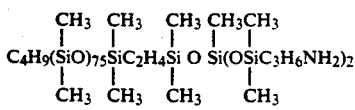

NH₂ group weight %: measured value=0.42%
(calculated value=0.53%)

EXAMPLE 4

The following were combined: 40 g polymer P-2 (SiH: 20.2 milliequivalents), 2.77 g (24.29 mmol) allyl glycidyl ether, and sufficient platinum/tetramethyl-divinyldisiloxane complex to give 20 ppm platinum metal referred to the preceding two reactants. After heating at 80°–90° C. for 2.5 hours, a sample was taken, and disappearance of the absorption characteristic of the SiH group was confirmed in infrared spectrochemical analysis. The low boilers were distilled off in vacuo with heating to afford a transparent liquid, which was confirmed by NMR, IR, and GPC analyses and determination of the epoxy group weight %, to be an organopolysiloxane with the following structural formula.

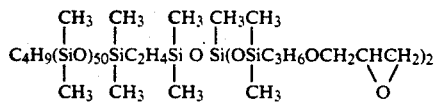

epoxy group weight %: measured value=1.92%
(calculated value=2.07%)

EXAMPLE 5

The following were combined: 40 g polymer P-2 (SiH: 20.2 milliequivalents), 5.71 g (22.26 mmol) trimethylsilyl undecenoate, and sufficient platinum/tetramethyldivinyldisiloxane complex to give 20 ppm platinum metal referred to the preceding two reactants. After heating at 90°–100° C. for 2 hours, a sample was taken, and disappearance of the absorption characteristic of the SiH group was confirmed in infrared spectrochemical analysis. The low boilers were distilled off in vacuo with heating to afford a transparent liquid, which was confirmed by NMR, IR, and GPC analyses to be an organopolysiloxane with the following structural formula.

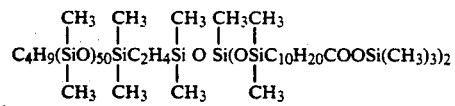

This organopolysiloxane (45 g) was stirred at 50° C. for 1 hour with 12.95 g methanol. The low boilers were then distilled off in vacuo with heating to afford a transparent liquid, which was confirmed by NMR, IR, and GPC analyses to be an organopolysiloxane with the following structural formula.

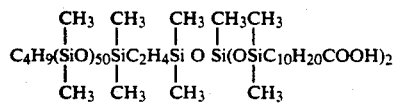

EXAMPLE 6

The following were combined: 40 g polymer P-2 (SiH: 20.2 milliequivalents), 3.16 g (24.29 mmol) trimethylallyloxysilane, and sufficient platinum/tetramethyldivinyldisiloxane complex to give 20 ppm platinum metal referred to the preceding two reactants. After heating at 80° C. for 2 hours, a sample was taken, and disappearance of the absorption characteristic of the SiH group was confirmed in infrared spectrochemical analysis. The low boilers were distilled off in vacuo with heating to afford a transparent liquid, which was confirmed by NMR, IR, and GPC analyses to be an organopolysiloxane with the following structural formula.

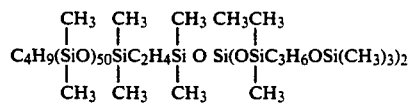

This organopolysiloxane (42 g) was mixed with 40 g methanol and 7 g propionic acid. While heating at ambient pressure, the trimethylmethoxysilane by-product was removed by distillation. When the temperature of the reaction mixture reached 80° C., heating was halted and the reaction mixture was returned to room temperature by cooling with water. The low boilers were distilled off in vacuo with heating to afford a transparent liquid, which was confirmed by NMR, IR, and GPC analyses and determination of the hydroxyl group weight %, to be an organopolysiloxane with the following structural formula.

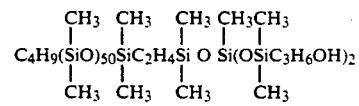

OH group weight %: measured value=0.79%
(calculated value=0.84%)

The organopolysiloxane according to the present invention is a novel compound, and the preparative methods according to the present invention characteristically provide this novel compound.

That which is claimed is:

1. An organopolysiloxane with the formula

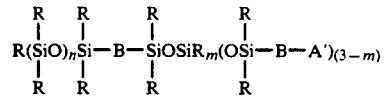

wherein R is a monovalent hydrocarbon group which is free of aliphatically unsaturated bonds and wherein the groups R may be identical or different; A' is selected from the group consisting of amino groups, carboxyl groups, hydroxyl groups, and epoxy-functional organic groups; B is the same or a different divalent organic group having at least 2 carbon atoms; m is zero or one; and n is an integer with a value of zero to 200.

2. A method for the preparation of an organopolysiloxane with the formula

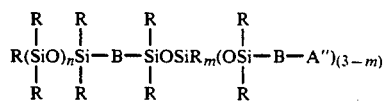

wherein R is a monovalent hydrocarbon group which is free of aliphatically unsaturated bonds and wherein the groups R may be identical or different; A" is selected from the group consisting of amino groups, the carboxyl group, and the hydroxyl group; B is the same or a different divalent organic group having at least 2 carbon atoms; m is zero or one; and n is an integer with a value of zero to 200;

said method being characterized by first conducting an addition reaction, in the presence of a hydrosilylation-reaction catalyst between an organopolysiloxane with the formula

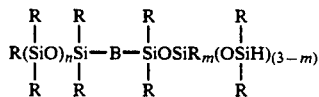

wherein R is a monovalent hydrocarbon group which is free of aliphatically unsaturated bonds and wherein the groups R may be identical or different, B is a divalent organic group having at least 2 carbon atoms, m is zero or one, and n is an integer with a value or zero to 200;

and an aliphatically unsaturated hydrocarbon compound which contains a triorganosilyl-blocked amino group, a triorganosilyl-blocked carboxyl group, or a triorganosilyl-blocked hydroxyl group, and by conducting a subsequent de-triorganosilylation reaction.

3. A method for the preparation of an organopolysiloxane with the formula

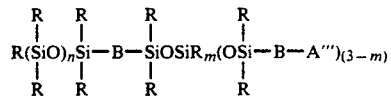

wherein R is a monovalent hydrocarbon group which is free of aliphatically unsaturated bonds and wherein the groups R may be identical or different, A''' is an epoxy-functional organic group, B is the same or a different divalent organic group having at least 2 carbon atoms, m is zero or one, and n is an integer with a value of zero to 200;

wherein said method is being characterized by conducting an addition reaction in the presence of a hydrosilylation-reaction catalyst between an organopolysiloxane with the formula

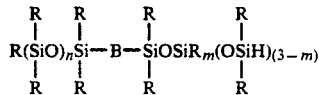

wherein R is a monovalent hydrocarbon group which is free of aliphatically unsaturated bonds and wherein the groups R may be identical or different, B is a divalent organic group having at least 2 carbon atoms, m is zero or one, and n is an integer with a value of zero to 200;

and an aliphatically unsaturated hydrocarbon compound which contains an epoxy-functional organic group.

* * * * *